United States Patent [19]

Muchel

[11] Patent Number: 4,669,839
[45] Date of Patent: Jun. 2, 1987

[54] OPTICAL SYSTEM FOR THERAPEUTIC USE OF LASER LIGHT

[75] Inventor: Franz Muchel, Königsbronn, Fed. Rep. of Germany

[73] Assignee: Carl-Zeiss-Stiftung, Heidenheim on the Brenz, Fed. Rep. of Germany

[21] Appl. No.: 654,239

[22] Filed: Sep. 24, 1984

[30] Foreign Application Priority Data

Oct. 1, 1983 [DE] Fed. Rep. of Germany ..... 33335810

[51] Int. Cl.⁴ .............................................. A61B 3/10
[52] U.S. Cl. .................................... 351/221; 351/205
[58] Field of Search ............... 351/205, 221, 216, 217, 351/218

[56] References Cited

U.S. PATENT DOCUMENTS

| | | | |
|---|---|---|---|
| 3,096,767 | 7/1963 | Gressez et al. | 351/221 X |
| 3,348,547 | 10/1967 | Kavanagh | 351/221 X |
| 3,703,176 | 11/1972 | Vassiliadis et al. | 351/221 X |
| 3,783,874 | 1/1974 | Koester et al. | 351/221 X |
| 3,840,289 | 10/1974 | Day | 351/174 |
| 3,914,032 | 10/1975 | Takano et al. | 351/206 |

FOREIGN PATENT DOCUMENTS 0089921 4/1983 European Pat. Off. .

*Primary Examiner*—Rodney B. Bovernick
*Attorney, Agent, or Firm*—Stonebaker, Shepard & Stephens

[57] ABSTRACT

A combined observation and laser therapy instrument having an optical system which is fully compensated for the difference in focus of the laser radiation and the observation light.

4 Claims, 3 Drawing Figures 41  42  43

61  62

OPTICAL SYSTEM FOR THERAPEUTIC USE OF LASER LIGHT

The present invention relates to an optical system for laser therapy and observation instruments in which there is means for relfecting the laser radiation into the observation ray path.

Laser light is used, for instance, for purposes of treatment of the eye. For example, U.S. Pat. No. 3,769,963 of Goldman et al., Nov. 6, 1973, discloses an instrument in which a laser light path is combined with an operation microscope, for laser treatment of the eye. However, in this instrument, the laser radiation is conducted outside the microscope; that is, the laser beam does not pass through the optics of the microscope.

For the sake of compactness of construction, it is desirable to conduct the laser radiation through the optical system of the observation instrument, i.e., through the operation microscope. However, if this is done, it results in a focusing problem. Because of the difference in wavelengths of the treatment light (laser light) and the observation light, considerable differences in focus occur for the wavelength regions used.

The object of the present invention is to provide an optical system which compensates for the difference in focus which occurs when an imaging optical system is used for different wavelength regions.

This object is achieved, according to the invention, by introducing the laser therapy beam into the path of the observation beam through a reflecting element located between the main objective and the eyepiece of the observtion instrument, and by providing a correction optical system located in front of the reflecting element as seen in the direction of observation (that is, between the eyepiece and the reflecting element), this correction optical system serving to compensate for the difference in focus between the laser light and the observation light.

An advantageous embodiment of the invention is constructed in accordance with the parameters stated below.

The advantages obtained by the invention include the fact that the laser radiation for therapeutic purposes can be conducted through the optical system of an ordinary commercial diagnostic instrument without having to tolerate any impairment in the image, and that the conducting of the laser radiation through the observation optical system makes possible a very small and compact construction of a laser therapy instrument.

BRIEF DESCRIPTION OF THE DRAWINGS

In the accompanying schematic or diagrammatic drawings.

DESCRIPTION OF A PREFERRED EMBODIMENT

Figure 1:
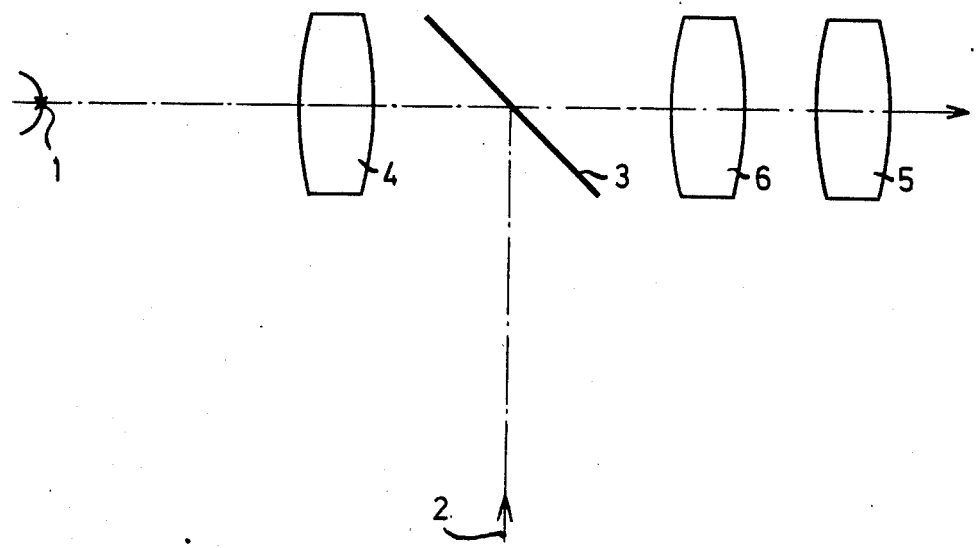
FIG. 1 is a diagram showing the general arrangement of the optical system of the invention within a diagnostic or observation instrument.

Referring now to FIG. 1, the object being examined (i.e., the eye of a patient) is indicated at 1. Radiation from a laser indicated schematically at 2 travels in the direction of the arrowhead to a reflecting element 3, such as a mirror, where it is deflected to pass leftwardly toward the eye 1 coaxially with the observation optical axis indicated by the horizontal dot-dash line. This observation optical axis represents the optical axis of a conventional observation instrument, such as, e.g., a surgical operation microscope or a slit lamp as used in ophthalmological examination. The reflecting element 3 is partially pervious to laser target-light radiation and to observation light from the conventional light source, not shown, which illuminates the eye 1 and is reflected back therefrom, so that the target light and the observation light may be observed through the conventional observation optical system 5 of a slit lamp, operation microscope, or other observation instrument by a surgeon or other observer.

According to the invention, a supplementary or correction optical system indicated schematically at 6 is located on the optical axis between the reflecting element 3 and the eyepiece or observation optical system 5, to compensate or correct for the difference in focus between the laser radiation and the observation light. Assuming that one wishes to use laser therapy radiation with a wavelength $\lambda_1$ of 1064 nm, and laser target-light radiation with a wavelength $\lambda_2$ of 633 nm, and an observation light in the visible spectrum range of 480 nm to 644 nm, good results are obtained when the main objective 4 is constructed substantially in accordance with the parameters indicated in Table I and the correction optical system 6 is constructed substantially in accordance with the parameters indicated in Table II.

In these tables, the customary notation commonly used in lens patents is employed. The radii of the respective surfaces are indicated by the letter r with a numerical subscript identifying the particular surface, numbered consecutively from front to rear. Thicknesses and spacings are shown by d with a numerical subscript, numbering both thicknesses and spacings in a single numerical sequence. The index of refraction of each element is shown in the column headed $n_d$, and the Abbe number of the element in the column headed $v_d$. As usual, positive radii indicate surfaces convex toward the front or concave toward the rear, and negative radii represents surfaces concave toward the front or convex toward the rear. A single r number for two adjacent elements, with no spacing between them, indicates surfaces in contact with each other, which may be cemented.

Figure 2:
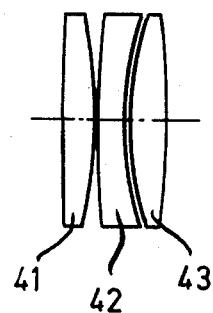
FIG. 2 is a diagram of a preferred form of the objective.
Figure 3:
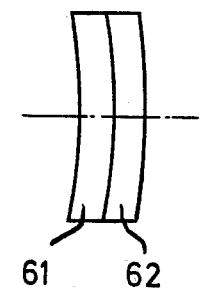
FIG. 3 is a diagram of a preferred form of the correction optical system.

FIG. 2 shows in detail the construction of the main objective shown only in general at 4 in FIG. 1. As seen in FIG. 2, it consists of three elements, respectively identified as 41, 42, and 43, the parameters of which are given in Table I. Similarly, the correction optical system, indicated in general at 6 in FIG. 1, is shown in more detail in FIG. 3. It has two elements, respectively identified as 61 and 62, the parameters of which are given in Table II.

TABLE I

| Element | | | $n_d$ | $v_d$ |
|---|---|---|---|---|
| 41 | $r_1 = 486.97$ | | | |
| | | $d_1 = 7$ | 1.6209 | 60.3 |
| | $r_2 = -105.93$ | | | |
| | | $d_2 = 0.3$ | | |
| 42 | $r_3 = 427.81$ | | | |
| | | $d_3 = 4$ | 1.8052 | 25.4 |
| | $r_4 = 78.298$ | | | |
| | | $d_4 = 0.3$ | | |
| 43 | $r_5 = 79.719$ | | | |
| | | $d_5 = 7.7$ | 1.5532 | 63.5 |
| | $r_6 = -227.12$ | | | |

TABLE I-continued

| Element | | $n_d$ | $v_d$ |
|---|---|---|---|
| | $s_1 = -119.4$ | | $s' = \alpha$ |

TABLE II

| Element | | | $n_d$ | $v_d$ |
|---|---|---|---|---|
| 61 | $r_1 = -137.25$ | | | |
| | | $d_1 = 7$ | 1.8052 | 25.4 |
| 62 | $r_2 = -91.07$ | | | |
| | | $d_2 = 7$ | 1.6177 | 49.8 |
| | $r_3 = -170.31$ | | | |
| | $s_1 = \alpha$ | | $s' = \alpha$ | |

With this construction, the objective 4 is corrected for the laser wavelength regions of 1064 nm and 633 nm, and the correction optical system 6 is corrected in such manner that, upon observation in the region of visible light (wavelengths 480 nm to 644 nm), the difference in focus which occurs as a result of the correction of the objective 4 is properly compensated. The combination of the main objective 4 with the correction optical system 6 is then also fully corrected for the wavelength region of 480 to 644 nm.

What is claimed is:

1. An instrument for combined observation of and laser treatment of a portion of a human body such as an eye, said instrument comprising:
    (a) a main objective;
    (b) an eyepiece;
    (c) said objective and eyepiece together defining an observation ray path along which visible observation light reaching said body may be reflected back from said body to said eyepiece;
    (d) a reflecting element located in said ray path between said objective and said eyepiece;
    (e) means for directing laser therapy radiation of one wavelength and laser target-light radiation of a different wavelength laterally to said reflecting element to be reflected thereby along said ray path toward said objective and to said body;
    (f) said main objective being substantially achromatized with regard to the respective wavelengths of said therapy radiation and said target-light radiation;
    (g) said eyepiece being a conventional eyepiece which is not achromatized with regard to the respective wavelengths of said visible observation light and said target-light radiation; and
    (h) a supplementary optical system located in said ray path between said reflecting element and said eyepiece;
    (i) said supplementary optical system in combination with said main objective serving to reduce chromatism of the combined beam of observation light and target-light radiation reflected back from said body to said eyepiece so that an improved image may be observed by an observer through said eyepiece.

2. The invention defined in claim 1, wherein said objective comprises elements dimensioned and arranged substantially in accordance with the following data:

| Element | | | $n_d$ | $v_d$ |
|---|---|---|---|---|
| 41 | $r_1 = 486.97$ | | | |
| | | $d_1 = 7$ | 1.6209 | 60.3 |
| | $r_2 = -105.93$ | | | |
| | | $d_2 = 0.3$ | | |
| 42 | $r_3 = 427.81$ | | | |
| | | $d_3 = 4$ | 1.8052 | 25.4 |
| | $r_4 = 78.298$ | | | |
| | | $d_4 = 0.3$ | | |
| 43 | $r_5 = 79.719$ | | | |
| | | $d_5 = 7.7$ | 1.5532 | 63.5 |
| | $r_6 = -227.12$ | | | |
| | $s_1 = 119.4$ | | $s' = \alpha$ | |

3. The invention defined in claim 1, wherein said supplementary optical system comprises elements dimensioned and arranged substantially in accordance with the following data:

| Element | | | $n_d$ | $v_d$ |
|---|---|---|---|---|
| 61 | $r_1 = -137.25$ | | | |
| | | $d_1 = 7$ | 1.8052 | 25.4 |
| 62 | $r_2 = -91.07$ | | | |
| | | $d_2 = 7$ | 1.6177 | 49.8 |
| | $r_3 = -170.31$ | | | |
| | $s_1 = \alpha$ | | $s' = \alpha$ | |

4. The invention defined in claim 1, wherein the therapy and observation instrument is designed for operation with laser therapy radiation of wavelength approximately 1064 nm and laser target-light radiation of wavelength approximately 633 nm and observation light of wavelength in the range of 480 nm to 644 nm, and wherein said objective comprises elements dimensioned and arranged substantially in accordance with the following data:

| Element | | | $n_d$ | $v_d$ |
|---|---|---|---|---|
| 41 | $r_1 = 486.97$ | | | |
| | | $d_1 = 7$ | 1.6209 | 60.3 |
| | $r_2 = -105.93$ | | | |
| | | $d_2 = 0.3$ | | |
| 42 | $r_3 = 427.81$ | | | |
| | | $d_3 = 4$ | 1.8052 | 25.4 |
| | $r_4 = 78.298$ | | | |
| | | $d_4 = 0.3$ | | |
| 43 | $r_5 = 79.719$ | | | |
| | | $d_5 = 7.7$ | 1.5532 | 63.5 |
| | $r_6 = -227.12$ | | | |
| | $s_1 = -119.4$ | | $s' = \alpha$ | | and said supplementary optical system comprises elements dimensioned and arranged substantially in accordance with the following data:

| Element | | | $n_d$ | $v_d$ |
|---|---|---|---|---|
| 61 | $r_1 = -137.25$ | | | |
| | | $d_1 = 7$ | 1.8052 | 25.4 |
| 62 | $r_2 = -91.07$ | | | |
| | | $d_2 = 7$ | 1.6177 | 49.8 |
| | $r_3 = -170.31$ | | | |
| | $s_1 = \alpha$ | | $s' = \alpha$ | |

* * * * *